(12) United States Patent
Frati

(10) Patent No.: US 6,514,550 B1
(45) Date of Patent: Feb. 4, 2003

(54) METHOD AND SYSTEM FOR CARRYING OUT THE DISINFESTATION OF PRODUCTS BY MEANS OF THE USE OF GAS UNDER ATMOSPHERIC PRESSURE WITH PRETREATMENT IN VACUO

(75) Inventor: Maurizio Frati, Milan (IT)

(73) Assignee: L'Air Liquide Societe Anonyme a Directoire et Conseil de Surveillance Pour l'Etude et l'Exploitation des Procedes Georges Claude, Paris (FR)

(*) Notice: Subject to any disclaimer, the term of this patent is extended or adjusted under 35 U.S.C. 154(b) by 0 days.

(21) Appl. No.: 09/731,868

(22) Filed: Dec. 8, 2000

(30) Foreign Application Priority Data

Dec. 22, 1999 (IT) .......................................... MI99A2686

(51) Int. Cl.$^7$ ................................................. A23B 4/16
(52) U.S. Cl. ......................... 426/320; 426/418; 426/419
(58) Field of Search ................................. 426/320, 418, 426/419

(56) References Cited

U.S. PATENT DOCUMENTS 3,897,210 A * 7/1975 Gruber et al. ............... 426/320
6,123,969 A * 9/2000 Sjoberg ....................... 426/418

* cited by examiner

*Primary Examiner*—Helen Pratt
(74) *Attorney, Agent, or Firm*—Burns, Doane, Swecker & Mathis, L.L.P.

(57) ABSTRACT

A method and system for carrying out the disinfestation of a product by means of the use of disinfesting gas under atmospheric pressure with pretreatment in vacuo, the said product being introduced into a first container in which the vacuum is produced and in which, subsequently, the said vacuum is broken by the introduction of the disinfesting gas, the said method comprising: a) the introduction of the first container into a second container before the vacuum is produced, b) the creation of the vacuum in both containers and the subsequent breaking of the said vacuum by passing the disinfesting gas into the two containers, c) the removal of the said gas from the second container, the gas being retained in the first container, d) the extraction of the first container from the second container so as to permit the use of the latter for subsequent disinfestation, the disinfesting gas being retained in the first container for the time necessary to complete the disinfestation of the product.

6 Claims, 2 Drawing Sheets

METHOD AND SYSTEM FOR CARRYING OUT THE DISINFESTATION OF PRODUCTS BY MEANS OF THE USE OF GAS UNDER ATMOSPHERIC PRESSURE WITH PRETREATMENT IN VACUO

The present invention relates to a method according to the preamble of the main claim. The invention further relates to an system for carrying out the method referred to above in accordance with the preamble of the appropriate independent claim.

As is known, many methods exist for disinfesting the most varied types of products, food products or otherwise, by using appropriate gases, in particular $CO_2$ and $N_2$, argon or toxic gases.

All methods presently known operate under variable pressure conditions, such as in vacuo, under atmospheric pressure or under superatmospheric pressure; depending on the various operating conditions, various types of apparatus with various degrees of complexity and cost are employed to implement these methods. The use of one of the abovementioned known methods depends, in particular, on the product to be treated.

As an example of the above, we now consider the disinfestation of a manufactured wooden article infested with woodworm or of plant products, such as medicinal herbs and the like, compressed in their containers. Since, in the case of the manufactured wooden article, the woodworm bores channels within the ligneous structure, and in the case of compressed plant products the infesting agent may be present in holes within the body of the product, in order to ensure that the insect comes into contact with the disinfesting gas it is possible, according to a first method, to introduce the manufactured article into an atmosphere containing the disinfesting gas and wait until the latter penetrates to the interior of the channel by diffusion or, if the gas used has a specific gravity substantially greater than that of air, by gravity.

This known operating method is relatively simple and gives rise to restricted costs; however, it also presents various not inconsiderable disadvantages, included among which are the excessively long treatment times and the impossibility of completely replacing the ambient air within the channels or holes with disinfesting gas. In this context, for example, we may consider a channel which is formed vertically, where the open end is at the bottom: in this case, it is virtually impossible for a disinfesting gas which is heavier than air, such as for example $CO_2$ or argon, to fill the channel completely and eliminate the infesting agent in whatever position it may be located. Consequently, the infesting agent survives where it does not come into contact with the disinfesting gas.

This known method, then, is of limited efficacy although it is carried out with a system using apparatus of limited cost.

In order to eliminate the disadvantages of the known method of disinfesting products, as described above, other methods are known as alternatives to that described previously.

One of these methods comprises carrying out the disinfestation by first creating, in a container in which the product under treatment is placed, first a high vacuum and then a partial vacuum obtained by breaking the high vacuum with the disinfesting gas. This is performed in the same container (or cell) in which the product is placed, this container being produced in a manner capable of resisting the vacuum throughout the period necessary to complete the disinfestation.

According to another known method, by contrast, disinfestation is carried out by placing the product in an appropriate cell, into which disinfesting gas (usually $CO_2$) is introduced, for a predetermined period, under a pressure greater than atmospheric pressure.

With both of these last two known methods, the disinfesting gas or vapour penetrates into all the cavities of the manufactured article to be treated, thus permitting effective disinfestation. However, these methods are carried out using systems of very high cost, particularly in view of the mechanical performance required of the apparatus involved (in the former case, cells capable of maintaining the vacuum for some days; in the latter, cells under an operating pressure of, customarily, 20 bar).

An object of the present invention is to provide a method of disinfesting a product and an appropriate system for its implementation which make it possible to overcome the disadvantages of the known equivalent methods and systems.

In particular, it is an object of the invention to provide a method of the stated type which permits efficacious disinfestation of the products and, at the same time, offers more limited costs of implementation than those of the equivalent previously known methods.

Another object is to provide a system for the implementation of the abovementioned method which entails lower costs and is less complex than the similar known systems.

BRIEF DESCRIPTION OF THE DRAWINGS

For greater ease of understanding of the present invention, there is attached, purely by way of example and without limiting effect, the drawing that follows, in which.

Figure 1:
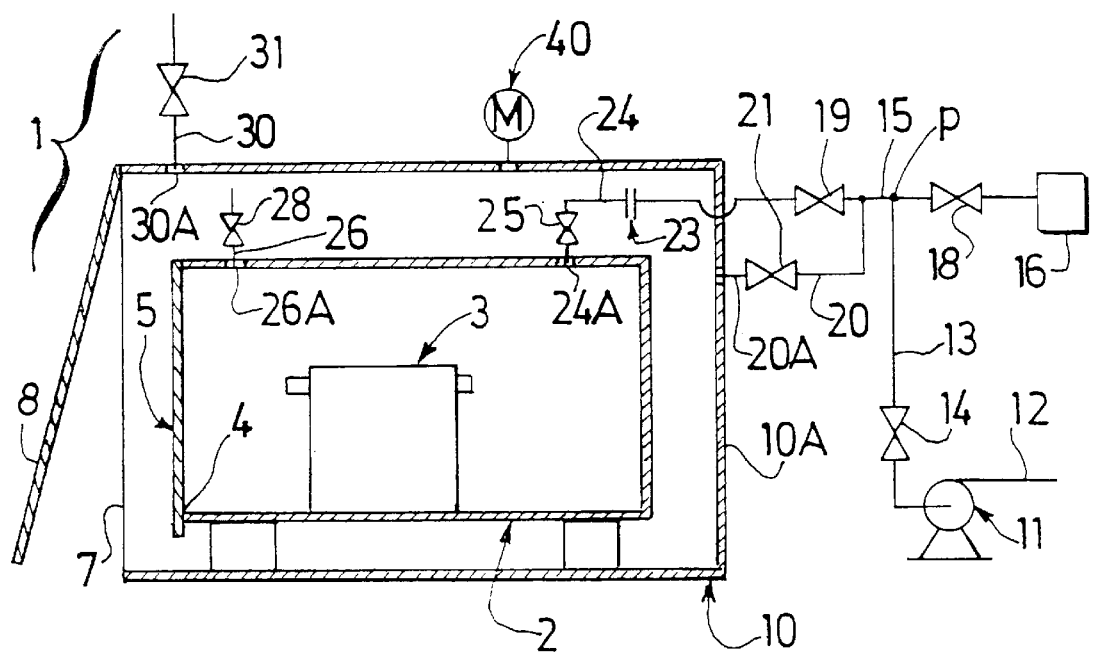
FIG. 1 shows a diagrammatic view of a system according to the invention.

With reference to the said figures, there is shown therein a system 1 for the implementation of the method according to the invention in which a first container 2 is "treated", this container being capable of containing a product 3 to be subjected to disinfestation by means of the use of a disinfesting gas such as $CO_2$, $N_2$ or argon. This gas may, if appropriate, be humidified to allow the product 3, during the disinfesting treatment, to be subjected to a suitable relative humidity.

The container 2 possesses optimum gas-tightness, but need not necessarily meet particular requirements in terms of mechanical strength, such as resistance to vacuum or elevated pressure. By way of example, a container suitable for the purpose may be a container made from rigid or even flexible polymeric or metal materials, such as bags or the like, produced, by way of example and without restricting more general cases, from one or more layers or polyethylene. As stated, this container may be in the shape of a bag (as in FIG. 2) or a parallelepiped (as in FIGS. 1 and 2).

Obviously, the container 2 is provided with an aperture 4 for the introduction therein of the manufactured article or product (food product or otherwise) to be subjected to disinfestation. This container is also provided with suitable and known closure means 5 for the said aperture (not shown) which guarantee good tightness to the disinfesting gas (which, as will be described, is introduced into the container).

As shown in FIG. 1, the system 1 comprises a second container 10 capable of accommodating the first container 2 (or plurality of containers 2) and provided with an aperture 7 on which a closure port or member 8 is attached.

In this case, also, known sealing means are provided in association with the closure member 8.

The second container 10 possesses the mechanical strength requirements necessary to resist the vacuum. This container or cell is, for example, made from steel or another metal material. It also possesses optimum tightness to the disinfesting gas which, as will be described, is introduced therein.

The system 1 further comprises a vacuum pump 11 connected to a pipe or line 12 for the evacuation of the air or gas, opening to atmosphere or into a suitable gas collection member. The pump is further connected to a pipe or line 13 on which is provided a valve member 14; the line 13 is connected to a line 15 which is connected to a tank or source 16 (known per se) of flushing or disinfesting gas (for example, $CO_2$). In particular, the line 13 is connected to the line 15 (at the connection point P) in a position between two valve members 18 and 19; connected to the line 15 between the connection point P and the valve member 19 is a line 20 (provided with its own valve member 21) connected to the container 10 and opening into the latter at 20A.

The line or pipe 15 penetrates (by a known method and in a sealed manner), through its wall 10A, into the second container 10 and is connected by means of an openable connecting member 23 (for example, a flange) to a line or pipe 24 connected to the first container 2 and opening into the latter through a mouth 24A thereof. A valve member 25 is provided on the line 24. Also connected to the container 2 is a pipe 26 opening into the container 2 through its mouth 26A; a valve member 28 is provided on the pipe 26. The pipe 26 is opened downstream of the member 26A and serves for the manual decontamination of the container 2.

A similar pipe 30 is associated with the second container 10; it is provided with a valve member 31, opens into the container 10 at 30A and is interrupted downstream of the member 31.

Finally, a manometer 40 is connected to the container 10 and measures the internal pressure therein.

It is now necessary to disinfest the product 3 previously placed in the container 2, the closure means 5 of the latter being closed. The container 2, after closure of the valve member 28 and opening of the valve member 25, is placed in the container or cell 10 connected to the connecting member 23, and the closure port or member 8 is closed. The valve member 31 is then closed and the members 14, 19 and 21 are opened.

At this point, the vacuum pump 11 is activated and allowed to remain active until the manometer 40, indicating the pressure within the container 10, indicates the desired value, which in general, though without this constituting a limitation, is 0.01–0.03 bar absolute pressure. The effect of the connections made is that the degree of vacuum prevailing in the container 10 is the same as that prevailing in the container 2 and therefore acting on the manufactured article or product 3.

The valve member 14 is now closed and the vacuum is broken by the introduction of disinfesting gas into the containers 2 and 10 by means of the gradual opening of the valve member 18; the vacuum is thus broken until the pressure within the container 10 equals the external pressure, and it is at this point that the valve members 18 and 19 are closed.

At this stage of the process, the product is immersed in a disinfesting gas atmosphere which, because of the vacuum created, reaches all the cavities in the manufactured article, thus bringing the infesting agents, wherever they are located, into contact with the disinfesting gas.

The next stage is to remove the disinfesting gas present in the space between the containers 2 and 10 in order to allow the opening of the member 8 and so be able to remove the container 2 with the associated product 3 from the container or cell 10.

For decontamination, the valve members 14 and 31 are opened (the valve member 21 is still open from the previous implementing stage of the method) and the vacuum pump 11 is activated, the intervening space between the containers 2 and 10 thus being flushed with ambient air entering, via the valve member 31, into the container 10.

It should be noted that, preferably, during the decontamination operation, the pressure in the container 10 must not be less than the external pressure of a value equal to approximately 0.0005 bar; this is to avoid excessive mechanical stresses on the container 2.

Decontamination, when complete, may be verified by means of appropriate analysis, using known methods, of the air issuing from the line 12. On completion, it is possible to open the cell or container 10 and remove therefrom the container 2, which must remain closed for the time considered necessary in order for the gas to complete its disinfesting action.

The removal of the container 2 from the container 10 frees the abovementioned container 10, which can thus be reused for other, subsequent disinfestation operations without its being necessary to wait for the operation in the container 2 to be completed over the (long) periods that are required and necessary. The method according to the invention thus allows the preparation of a plurality of containers 2 in which disinfestation of a product is carried out without its being necessary to wait for the end of the long waiting periods necessary for the latter procedure to be completed. Furthermore, any disinfestation operation always requires the use of the same container or cell 10 in which one or more containers 2 accommodating the product to be disinfested are placed. The latter, as stated, are containers of much lower cost than the container 10 (since they need not be produced so as to have any particular mechanical resistance to vacuum or superatmospheric pressure), as a result of which the implementation of the method according to the invention entails more limited costs (referring to the costs of the system—comprising a single cell 10 for a plurality of containers 2—and apparatus) by comparison with the costs of implementing the known methods.

Figure 2:
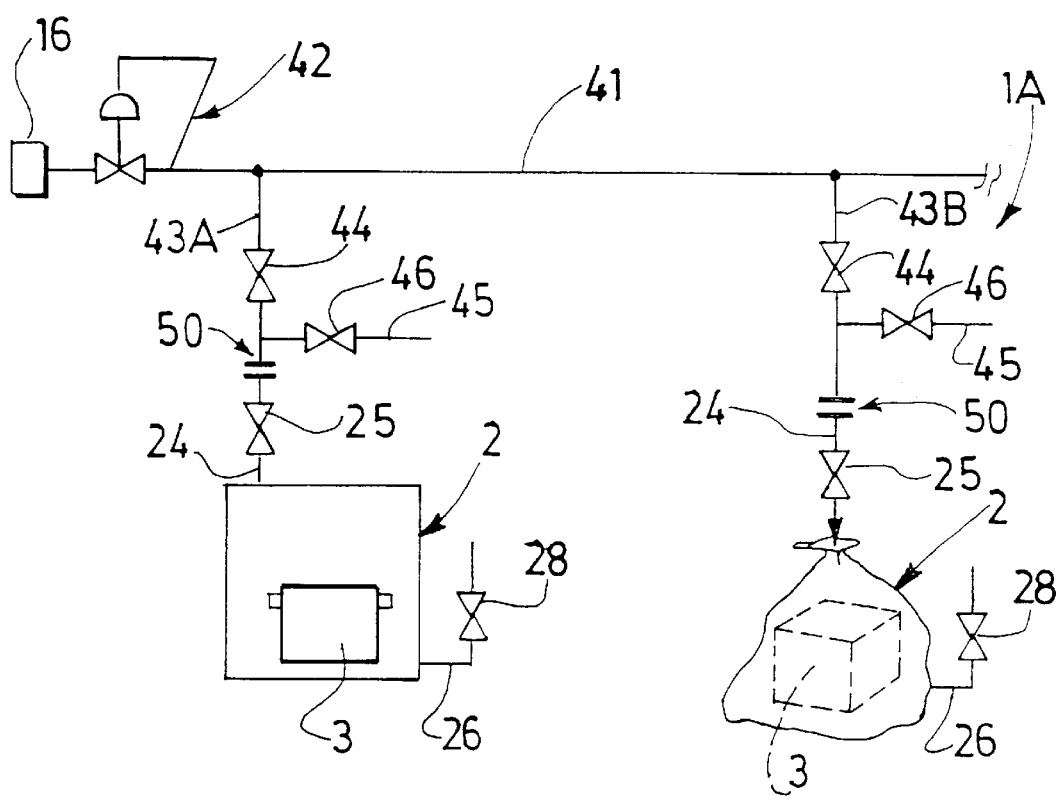
FIG. 2 shows part of the system according to FIG. 1, not shown in the latter figure.

Returning to the method described above, the valve element 25 is closed, the member 23 is disconnected and the container 2 is removed from the container or cell 10 and can be simply placed in storage pending completion of the disinfestation or connected to the system portion 1A shown in FIG. 2 (in which parts corresponding to those in FIG. 1 are indicated by the same reference numbers). Storage takes place if the container is of the type which provides complete tightness to the disinfesting gas; conversely if that tightness cannot be guaranteed, the container 2 is connected to the portion 1A of the system 1 so as to be subjected to a slight internal pressure (of between 0.0001 and 0.0005 bar above atmospheric pressure) by means of connection with the appropriate line 43A. This connection ensures that, in the presence of a leak, no ambient air enters into the container, but, at most, the disinfesting gas exits into the environment.

The part 1A of the system comprises a line or pipe 41 connected to the disinfesting gas tank 16. Provided on this line is a pressure reducer 42 which has the task of maintaining the line under the desired pressure.

Connected to the line 41 are one or more lines or pipes 43A, 43B, etc. (only two pipes 43A and 43B are shown in FIG. 2) to which the containers 2 removed from the container 10 may be connected. Each line 43A, 43B, etc. comprises a basic or main valve 44 and an evacuation branch or line 45 on which a valve member 46 is provided. Each line, furthermore, can be connected via a connecting member 50 (for example, a flange, holding ring or the like) to the line or pipe 24 associated with the container 2.

In order to obtain slight pressurization of the containers 2, the latter are connected (by means of the members or flanges 50) to the lines 43A, 43B. Each appropriate basic valve 44 is then opened, and then the associated valve 46 is opened. The latter is left open for some seconds and then closed again. In this manner, any air present in each line 43A, 43B, etc. is removed, the line being flushed with the disinfesting gas and any air thus being prevented from entering into the containers 2.

Each line 24 is then connected to the corresponding line 43A, etc., the valve member 25 being opened; in this way, the gas passes into the container 2 from the line 41 under slight excess pressure.

Each container is kept connected to the line 41 until the end of the period necessary for the disinfestation of the product located therein; subsequently, after that period has expired, the valve members 44 and 25 are closed, and the containers 2 are detached from the lines 43A, 43B, etc. The disinfesting gas is then evacuated from each container 2, the valve members 25 and 28 simply being opened or the container 2 being decontaminated by means of an air flow, using known methods.

By virtue of the invention, optimum disinfestation of a plurality of products is achieved in substantially shorter periods than can be attained using known methods and at higher [sic] costs than the latter.

The system 1 may be fully automated and controlled by control units of microprocessors.

What is claimed is:

1. Method for carrying out the disinfestation of a product by use of a disinfesting gas under atmospheric pressure with pretreatment in vacuo, the product being introduced into at least one first container in which the vacuum is produced and in which, subsequently, the vacuum is broken by the introduction of the disinfesting gas, the method comprising:
    a) introducing the at least one first container into a second container before the vacuum is produced;
    b) simultaneously creating the vacuum in all of the containers and, subsequently, simultaneously breaking the vacuum by passing the disinfesting gas into the containers;
    c) removing the gas from the second container wherein the gas is retained in the at least one first container present in the second container; and
    d) extracting the at least one first container from the second container so as to permit the use of the second container for subsequent disinfestation of a product contained in at least one other container.

2. Method according to claim 1, further comprising placing the first container in storage after removal from the second container.

3. Method according to claim 1, further comprising connecting the first container, after removal from the second container, to a line or pipe in which the disinfesting gas is present under slight excess pressure relative to atmospheric pressure.

4. Method according to claim 3, wherein the gas under excess pressure is at a pressure greater than atmospheric pressure by a value of between 0.0001 and 0.0005 bar.

5. Method according to claim 1, wherein during disinfestation of the second container, the difference between pressure in the second container and external atmospheric pressure is less than or equal to 0.0005 bar.

6. Method according to claim 1, further comprising removing air from the second container and monitoring the air to verify that its disinfestation has taken place, wherein the at least one first container is removed from the second container after the disinfestation has been verified.

* * * * *